(12) United States Patent
Van Dyke (10) Patent No.: US 6,514,955 B1
(45) Date of Patent: Feb. 4, 2003

(54) MULTI-FACETED METHOD TO REPRESS REPRODUCTION OF LATENT VIRUSES IN HUMANS AND ANIMALS

(75) Inventor: Knox Van Dyke, Morgantown, WV (US)

(73) Assignee: HIV Diagnostics, Inc., Lexington, KY (US)

( * ) Notice: Subject to any disclaimer, the term of this patent is extended or adjusted under 35 U.S.C. 154(b) by 0 days.

(21) Appl. No.: 08/475,791

(22) Filed: Jun. 7, 1995

Related U.S. Application Data (60) Division of application No. 08/317,730, filed on Oct. 4, 1994, now Pat. No. 5,686,436, which is a continuation-in-part of application No. 08/061,573, filed on May 13, 1993, now abandoned.

(51) Int. Cl.[7] .................. A61K 31/56; A61K 31/43; A61K 31/425; A61K 31/195
(52) U.S. Cl. .................. 514/171; 514/198; 514/369; 514/374; 514/378; 514/561; 514/563
(58) Field of Search .................. 424/450; 514/167, 514/171, 198, 369, 374, 378, 561, 563

(56) References Cited

U.S. PATENT DOCUMENTS 5,403,834 A * 4/1995 Malfroy-Camine ......... 514/185
5,463,063 A * 10/1995 Muller ....................... 546/201

FOREIGN PATENT DOCUMENTS

| EP | 269017 | 6/1988 |
|---|---|---|
| FR | 2699821 | 7/1994 |
| WO | 8901772 | 3/1989 |
| WO | 9116034 | 10/1991 |
| WO | 9221368 | 12/1992 |
| WO | 9402036 | 2/1994 |

OTHER PUBLICATIONS

Supplementary Partial European Search Report.
AIDS Research and Human Retroviruses, vol. 9, No. 4, 1993, "Antioxidants Inhibit Stimulation of HIV Transcription", Mary Ann Liebert, Inc., Publishers.
Schreck, R. and Baeuerle, P.A., NF–Kappa–B as Inducible Transcriptional Activator of the Granulocyte–Macrophage Colony–Stimulating Factor Gene, Molecular and Cellular Biology, 10(3):1281–1286, Mar. 1990.
Greenspan, D., Greenspan, J.S., Schiodt M., and Pindborg, J.J., AIDS and the Mouth, Munksgaard Publishing, Distributed by Mosby–Year Book, Inc., Chicago, IL, References to: Chapter 4—Human Immune Deficiency Viruses and Chapter 5—Animal Models for AIDS, 1990.
Schreck, R., Rieber, P., and Baeuerle, P.A., Reactive Oxygen Intermediates as Apparently Widely used Messengers in the Activation of the NF–Kappa–B Transcription Factor and HIV–1, EMBO J. 10(8):2247–2258, 1991.

(List continued on next page.)

*Primary Examiner*—Gollamudi S. Kishore
(74) *Attorney, Agent, or Firm*—Price, Heneveld, Cooper, DeWitt & Litton (57) ABSTRACT

Disclosed are methods for repressing reproduction of latent viruses, such as HIV, in animals by the generally concurrent administration of (1) antioxidants including a glutathione agent; and (2) an NFKB induction inhibitor. Also disclosed are pharmaceutical compositions and kits for use in repressing reproduction of latent viruses such as HIV.

10 Claims, 3 Drawing Sheets

OTHER PUBLICATIONS

Lenardo, M.J., Baltimore, D., NF–Kappa–B: A Pleiotropic Mediator of Inducible and Tissue–Specific Gene Control, Cell, vol. 58, pp. 227–229, Jul. 28, 1989.

Radi, R., Cosgrove, T.P., Beckman, J.S., and Freeman, B.A., Peroxynitrite–induced Luminol Chemiluminescence, J. Biochem, 290: 51–57, 1993.

Agostini, C., Trentin, L., Zambello, R., and Semenzato, G., HIV–1 and the Lung, Am. Review of Respirable Disease, 147:1038–1049, 1993.

Meltzer, M.S. and Gendelman, H.E., Mononuclear Phagocytes as Targets, Tissue Reservoirs, and ImmunoRegulatory Cells in Human Immunodeficieny Virus Disease, Current Topics in Microbiology and Immunology, 181:239–264, 1992.

Grimm, S., and Baeuerle, P.A., The Inducible Transcription Factor NF–Kappa–B: Structure–Function Relationship of its Protein Subunits, Biochem. J. 290:297–308, 1993.

Segal, A.W. and Abo, A., The Biochemical Basis of the NADPH Oxidase of Phagocytes, Trends in Biol. Sci. 18:43–47, 1993.

Wang, J.F., Komarov, P., Sies, H., and Groot, H.D., Contribution of Nitric Oxide Synthase to Luminol–Dependent Chemiluminescence Generated by Phorbol–Ester–Activated Kupffer Cells, Biochem. J. 279:311–314, 1991.

Cathcart, R.F., III, Vitamin C in the Treatment of Acquired Immune Deficiency Syndrome (AIDS), Medical Hypothesis 14:423–433, 1984.

Mufson, R.A., Myers, C., Turpin, J.A., and Meltzer, M., Phorbol Ester Reduces Constitutive Nuclear NF–Kappa–B and Inhibits HIV–1 Production in Mature Human Monocytic Cells, J. of Leukocyte Biology, 52:637–644, Dec. 1992.

Van Dyke, K., Drug Therapy in Acquired Immunodeficiency Syndrome (AIDS), Modern Pharmacology 4th Edition, Chapter 55:1–15.

Magnani, M., Rossi, L., Brandi, G., Schiavano, G., Montroni, M. and Piedimonte, G., Targeting Antiretroviral Nucleoside Analogues in Phosphorylated Form to Macrophages: In Vitro and in Vivo Studies, Proc. Natl. Acad. Sci. USA., 89:6477–6481, Jul. 1992.

Baeuerle, P.A., The Inducible Transcription Activator NF–Kappa–B: Regulation by Distinct Protein Subunits, Bochimica et Biophysica Acta, 1072:63–80, 1991.

Sherman, M.P., Aeberhard, E.E., Wong, V.Z., Griscavage, J.M., and Ignarro, L.J., Pyrrolidine Dithiocarbamate Inhibits Induction of Nitric Oxide Synthase Activity in Rat Alveolar Macrophages, Biochemical and Biophysical Research Communications, 191(3):1301–1308, Mar. 31, 1993.

Dorseuil, O., Vazquez, A., Lange P., Bertoglio, J., Gacon, G., Leca, G., Inhibition of Superoxide Production in B Lymphocytes by Rac Antisense Oligonucleotides, J. of Biol, Chem., 267(29):20540–20542, 1992.

Winkler, B.S., Orselli, S.M., and Rex, T.S., The Redox Couple Between Glutathione And Ascorbic Acid: A Chemical And Physiological Perspective, Free Radical Biology & Medicine, vol. 17, No. 4, pp. 333–335, 1994.

Author Unknown, Andrenocortical Steroids, p. 1451, p. 1447, p. 1449, not dated.

Product Brochure from Cite Technical Service: CITE® Probe™, CITE® Combo: Interpretation, 1 page, (not dated).

Roederer, M., Ela, S.W., Staal, F.J.T., Herzenberg, L.A., Herzenberg, L.A., N–Acetylcysteine: A New Approach to Anti–HIV Therapy, Aids Research And Human Retroviruses, vol. 8, No. 2, 1992.

Dandekar, S., Beebe, A.M., Barlough, J., Phillips, T., Elder, J., Torten M., Pedersen, N., Detection of Feline Immunodeficiency Virus (FIV) Nucleic Acids in FIV–Seronegative Cats, Journal of Virology, pp. 4040–4049, Jul., 1992.

White, A.C., Thannickal, V.J., Fanburg, B.L., Glutathione Deficiency in Human Disease, J. Nutr. Biochem., vol. 5, pp. 218–226, May, 1994.

Legrand–Poels, S., Vaira, D., Pincemail, J., De Vorst, A.V., Piette, J., Activation of Human Immunodeficiency Virus Type 1 by Oxidative Stress, AIDS Research And Human Retroviruses, vol. 6, No. 12, pp. 1389–1397, 1990.

Author Unknown, Questions & Answers about Sustained Release ONDROX™ Multi–Antioxidant Formulation, Unimed, Inc., 4 pages, 1992.

Halliwell, B. and Cross, C.E., Reactive Oxygen Species, Antioxidants and Acquired Immunodeficiency Syndrome, Arch Inter. Mod., vol. 151, pp. 29–31, Jan., 1991.

Bergamini, A., Capozzi, M., Ghlbeth, L., Olnl, L., Salanitro, A., Milanese, G., Wagner, T., Beninate, B., Peace, C.D., Amici, C., Rocchi, G., Cystamine Potently Suppresses In Vitro HIV Replication in Acutely and Chronically Infected Human Cells, J. Clin. Invest., vol. 93, pp. 2251–2257, May, 1994.

Barnes, P.J., Adcock, I., Anti–Inflammatory Actions of Steroids: Molecular Mechanisms, Tips Reviews, vol. 14, pp. 436–441, Dec., 1993.

Sodora, D.L., Shpaer, E.G., Kitchell, B.E., Dow, S.W., Hoover, E.A., Mullins, J.I., Identification of Three Feline Immunodeficiency Virus (FIV) env Gene Subtypes and Comparison of the FIV and Human Immunodeficiency Virus Type 1 Evolutionary Patterns, Journal of Virology, vol. 68, No. 4, pp. 2230–2238, Apr. 1994.

O'Neil, L. L., Burkhard, M. J., Diehl, L. J. and Hoover, E. A., "Vertical Transmission of Feline Immunodeficiency Virus", AIDS Research and Human Retroviruses, vol. 1, No. 1, pp. 171–182, 1995.

Zaccaro, L., Falcone, M. L., Silva, S., Bigalli, L., Cecchettini, A., Giorgi, F., Malvaldi, G. and Bendinelli, M., "Defective Natural Killer Cell Cytotoxic Activity in Feline Immunodeficiency Virus–Infected Cats", AIDS Research and Human Retroviruses, vol. 11, No. 6, pp. 747–752, 1995.

Witschi, A., Junker, E., Schranz, C., Speck, R. F. and Lauterburg, B. H., "Supplementation of N–Acetylcysteine Fails to Increase Glutathione in Lymphocytes and Plasma of Patients with AIDS", AIDS Research and Human Retroviruses, vol. 11, No. 1, pp. 141–143, 1995.

Essex, M., "The HIV–1 Vaccine Dilemma: Lessons From The Cat", The Journal of NIH Research, vol. 7, pp. 37–42, Mar., 1995.

Smyth, N.R., McCracken, C., Gaskell, R. M. , Cameron, J.M., Coates, J.A.V., Gaskell, C.J., Hart, C.A. and Bennett, M., "Susceptibility in Cell Culture of Feline Immunodeficiency Virus To Eighteen Antiviral Agents", Journal of Antimicrobial Chemotherapy, vol. 34, pp. 589–594, 1994.

Vitkovic, L., Stover, E. and Koslow, S.H., "Animal Models Recapitulate Aspects of HIV/CNS Disease", AIDS Research and Human Retroviruses, vol. 11, No. 6, pp. 753–759, 1995.

Song, W., Collisson, E.W., Li, J., Wolf, A.M., Elder, J. H., Grant, C.K., and Brown, W.C., "Feline Immunodeficiency Virus (FIV)–Specific Cytotoxic T Lymphocytes from Chronically Infected Cats Are Induced in Vitro by Retroviral Vector–Transduced Feline T Cells Expressing the FIV Capsid Protein", Virology 209, pp. 390–399, 1995.

Johnson, C.M., Torres, B.A., Koyama, H. and Yamamoto, J.K., "FIV as a Model for AIDS Vaccination", AIDS Research and Human Retroviruses, vol. 10, No. 3, pp. 225–228, 1994.

Bennett, M. and Hart, C. A., "Feline Immunodeficiency Virus Infection—A Model For HIV and AIDS?", J. Med. Microbiol., vol. 42, pp. 223–236, 1995.

Andrieu, J., Lu, W. and Levy, R., "Sustained Increases in CD4 Cell Counts in Asymptomatic Human Immunodeficiency Virus Type 1—Seropositive Patients Treated with Prednisolone for 1 Year", The Journal of Infectious Diseases, 171, pp. 523–530, 1995.

Clerici, M., Bevilacqua, M., Vago, T., Villa, M.L., Shearer, G.M., Norbiato, G., "An Immunoendocrinological Hypothesis of HIV Infection", The Lancet, vol. 343, pp. 1552–1553, Jun. 18, 1994.

Sibille, P., Avrameas, A., Moraillon, A., Richardson, J., Sonigo, P., Pancino, G., Strosberg, A.D., "Comparison of Serological Tests for the Diagnosis of Feline Immunodeficiency Virus Infection of Cats", Veterinary Microbiology, vol. 45, pp. 259–267, 1995.

Adis International, "Temporary Benefit of Zidovudine in Patients with AIDS", JACS, one page, Apr., 1994.

* cited by examiner

MULTI-FACETED METHOD TO REPRESS REPRODUCTION OF LATENT VIRUSES IN HUMANS AND ANIMALS

This is a division of application Ser. No. 08/317,730, filed on Oct. 4, 1994, by Knox (NMI) Van Dyke, for MULTI-FACETED METHOD TO REPRESS PRODUCTION OF LATENT VIRUSES IN HUMANS AND ANIMALS now U.S. Pat. No. 5,686,436.

This is a continuation-in-part application of application Ser. No. 08/061,573 filed on May 13, 1993 now abandoned. The present invention relates generally to a method for repressing the reproduction of latent viruses or retroviruses in humans and animals. Retroviruses are a class of viruses that replicate via a reverse flow of genetic information. For example, the present invention relates to, without limitation, a method for repressing the reproduction of latent viruses or retroviruses such as HIV-1, HIV-2, leukemia, Herpes I, II, and VI, and hepatitis A, B, C and D in man and certain animals.

BACKGROUND OF THE INVENTION

Acquired Immunodeficiency Syndrome (AIDS) is one of the most significant infections to appear in the last decade. This epidemic is not confined to a single segment of the population nor is its spread blocked by natural barriers or international boundaries. Millions have died in Africa and many more individuals are infected worldwide. In the United States more than 100,000 people have died and at least 1 million more are presently infected with the virus. This pandemic shows no signs of abating.

AIDS was first diagnosed in male homosexuals who exhibited a variety of infections of fungal (*Candida albicans*), protozoal (*Pneumocystis carinii*), and viral (*Herpes zoster*) origin. Many of these individuals also had an increased incidence of kaposi sarcoma and lymphoma. They had a depressed T helper/T suppressor lymphocyte cell ratio and an absence of delayed hypersensitivity responses. Collectively, these observations suggested a deficiency in cell-mediated immunity.

It is strongly suspected that the causative agent in AIDS is an RNA retrovirus called the human immunodeficiency virus (HIV-1 or HIV-2). HIV possesses an envelope glycoprotein (gp120) that has a high affinity for the $CD_4$ receptor on T helper cells and other target cells. These other target cells include bone marrow stem cells, macrophages, endothelial cells, glial cells, lymph node, dendritic cells, bowel enterochromaffin cells, cervical eptithlium and possibly Langerhans cells. However, it is the effects of HIV on T-helper cells that are the best known. The infectious process begins when the virus penetrates the body and enters the blood stream. Binding of HIV to $CD_4$ target cells involves interaction of the external envelope glycoprotein molecule gp120 with the $CD_4$ molecule, although other cell receptors may be involved. The virus next enters the target cell, or is internalized, through fusion of the viral envelope with the target cell membrane. Through this fusion, the virus loses its coat, and releases its RNA core and reverse transcriptase enzyme into the host cell cytoplasm.

The HIV reverse transcriptase enzyme copies the RNA message producing first a single-stranded, and then a double-stranded, DNA (circular complementary DNA). This newly formed double-stranded DNA becomes incorporated into the host chromosomal DNA once it enters the host cell nucleus. This incorporated viral DNA may remain dormant or, upon activation, will produce viral messenger RNA (mRNA). The viral mRNA codes for proteins that are important in viral replication. Glycoprotein will then envelop the RNA genome resulting in the production of infectious viral particles; completed viral particles are then released to infect other cells.

Greenspan, D. et al., "Aids and the Mouth," Chap. 4, pp. 50–51, Munksgaard Press, distributed by Mosby Year Book, Inc., Chicago, Ill., (1990), report that because the HIV DNA is integrated into the chromosomal DNA of the host target cell, the HIV DNA survives for the life of the infected cell. Thus, there may be a form of persistent infection where a few new HIV particles are produced with little, if any, killing of host cells. Greenspan et al. also report that the cells killed or inactivated are predominately $CD_4$ helper T cells with consequent loss in T-helper cell numbers, decrease in T4 helper/T8 suppressor cell ratios and reduction or loss of ability to mount a normal immune reaction, particularly in response to T cell dependent antigens such as those borne by viruses, fungi and encapsulated bacteria. Greenspan et al. also note that while other cells such as monocytes and macrophages are also infected, these cells are generally not killed and any functional defects which they incur from HIV infections are as yet not fully understood.

Schreck et al., *EMBO J.,* 10 (8):2247–2258, 1991, and Duh et al., *Proc. Nat'l. Acad. Sci.* (*USA*), 86:5974–5978, 1989, report that when using HIV infected Jurkat T lymphocyte cells, there is a factor inside the infected cells which controls transcription of certain nuclear genes of the host cell. This factor is formed of three proteins that bind together, namely, p50, p65 and I kappa B. Schreck et al. further report that normally the three proteins are formed in the target cell cytoplasm in this triad (three proteins bound together) in an inactive state. Under conditions such as oxidative stress, however, the viral reproducing mechanism is activated. The iKB factor is removed from the protein triad and the remaining p50, p65 complex becomes known as NF-kappa B (NFKB).

Schreck et al. have recognized that NFKB is a gene transcription factor that migrates into the nucleus of the HIV infected cell and switches on the production of the HIV virus of a virally infected cell. Schreck et al. also report that hydrogen peroxide and oxygen radicals are agents commonly produced during the inflammatory process and that micromolar concentrations of hydrogen peroxide can induce the expression of HIV-1 in a human T cell line. They further report that the expression of HIV is mediated by NFKB transcription factor which is potently and rapidly activated by a hydrogen peroxide treatment of cells from its inactive cytoplasmic form. They additionally report that N-acetyl cysteine and other thiol compounds block the activation of NFKB. They concluded that these diverse agents thought to activate NFKB by distinct intracellular pathways might act through a common mechanism involving the synthesis of reactive oxygen intermediates. They did not suggest any possible candidates for that reactive oxygen intermediate.

Sherman et al., *Biochem. Biophys. Res. Comm.,* 191 (3):1301–1308, 1993, report that pyrrolidine dithiocarbamate (PDTC) is an inhibitor of NFKB activation. They further report that this compound is an inhibitor of nitric oxide synthase (NO synthase). They further report that oxidative stress in HIV infection is manifested by decreased cysteine and glutathione levels in plasma and leukocytes. They suggest that the redox regulation of macrophages may be crucial to the activation of nitric oxide synthase and that PDTC may act as a scavenger of reactive oxygen species which prevents them from participation in the activation of NFKB.

Current approaches to HIV treatment generally involve immunotherapy (e.g., vaccines against whole killed HIV and a variety of HIV surface glycoproteins) directed at the HIV as well as pharmacological intervention in the fHIV infectious process. In theory, any of the steps of viral replication or release could be points of pharmacological attack against the virus. The major chemotherapeutic attack by available drugs has been at the level of inhibition of viral reverse transcriptase. The first drug licensed for use in HIV treatment became available in 1987; it was azidothymidine (AZT). In the early 1990's, dideoxyinosine (DDI) and dideoxycytidine (DDC) were approved by the FDA. AZT and DDI were approved for monotherapy while DDC is used in combination with one of the other drugs.

A basic problem of HIV research is that experiments aimed at killing the virus in vitro and in vivo appear to give opposite results. For example, AZT is very effective in vitro in killing the HIV virus. Valencia, E. et al., *Ann. Med. International*, 9, (11):531–537, 1992 and Baumgarten, R., *Dermatol-Monatsschr.*, 175, (8):469–473, 1989 report, however, that AZT does not prolong the lives of HIV infected victims to any great extent. Other drugs and biological therapies, such as antioxidant therapy, which have produced encouraging in vitro results, also have not proven effective in vivo as reported in the literature. [See, e.g., Cathcart, *Medical Hypothesis*, 14:423–433, 1984; Kappus and Diplock, *Free Radical Biol. and Med.*, 12:55–74, 1992; Muller, *Free Radical Biol. and Med.*, 13:651–657, 1992; Fuchs, *Medical Hypotheses*, 36:60–64, 1991; Roederer, *AIDS Res. and Human Retrovirus*, 8:209–217, 1992; Harakeh et al., *Proc. Nat'l. Acad. Sci.*, 87:7245–7249, 1990; Hersh et al., *JAMA*, 265:1538–1544, 1991; Staal, et al., *AIDS Research and Human Retrovirus*, 8:305–309, 1992.]

Many different treatment regimens are and have been used to treat the HIV infection and AIDS which occurs after the latent infection. While they might prolong survival and possibly minimize symptoms, in view of the mounting worldwide concern regarding the epidemic, these treatments have not been generally successful. Therefore, the continuing hard reality is that once the virus enters the body and begins the uncoating process, a fatal outcome is almost inevitable. Such an outcome reveals the continuing need for additional research to discover a method of treatment which can suppress the reproduction of latent viruses such as HIV.

SUMMARY OF THE INVENTION

The present invention provides methods and pharmaceutical compositions for repressing reproduction of latent viruses, such as HIV, in humans and animals, by the generally concurrent administration of 1) a glutathione agent; 2) at least one additional antioxidant; and 3) at least one NFKB induction inhibitor. Further aspects and advantages of the invention will be apparent to those skilled in the art upon review of the following detailed description taken in conjunction with the appended claims.

DETAILED DESCRIPTION OF THE INVENTION

Introduction

There are several different preferred embodiment methods to repress reproduction of latent viruses in humans and animals. (For the remainder of the detailed description of the invention and including the claims, the term "animal" refers to all animals including humans.) All the methods share the common feature of administering (1) a glutathione precursor, a glutathione production enhancer, or glutathione, (2) high doses of additional fat- and water-soluble antioxidants, and (3) an NFKB induction inhibitor, to an animal infected with a latent virus. The fat- and water-soluble antioxidants are administered to an animal infected with a latent virus to assist in the maintenance in a reduced electrical state of the animal's glutathione. Glutathione or a glutathione precursor are also administered to an animal infected with a latent virus to maintain or bolster the animal's natural levels of glutathione. It has been surprisingly found that by using this combination of ingredients, the reproduction of latent viruses in animals can be repressed.

Additional ingredients which can be used include the peroxynitrite production suppressor NADPH inhibitor, an effective amount of a superoxide anion radical reducing agent, NO•reducing agents and xanthine oxidase inhibitors. Alternatively, various combinations of these peroxynitrite production inhibitors can be used.

Figure 1:
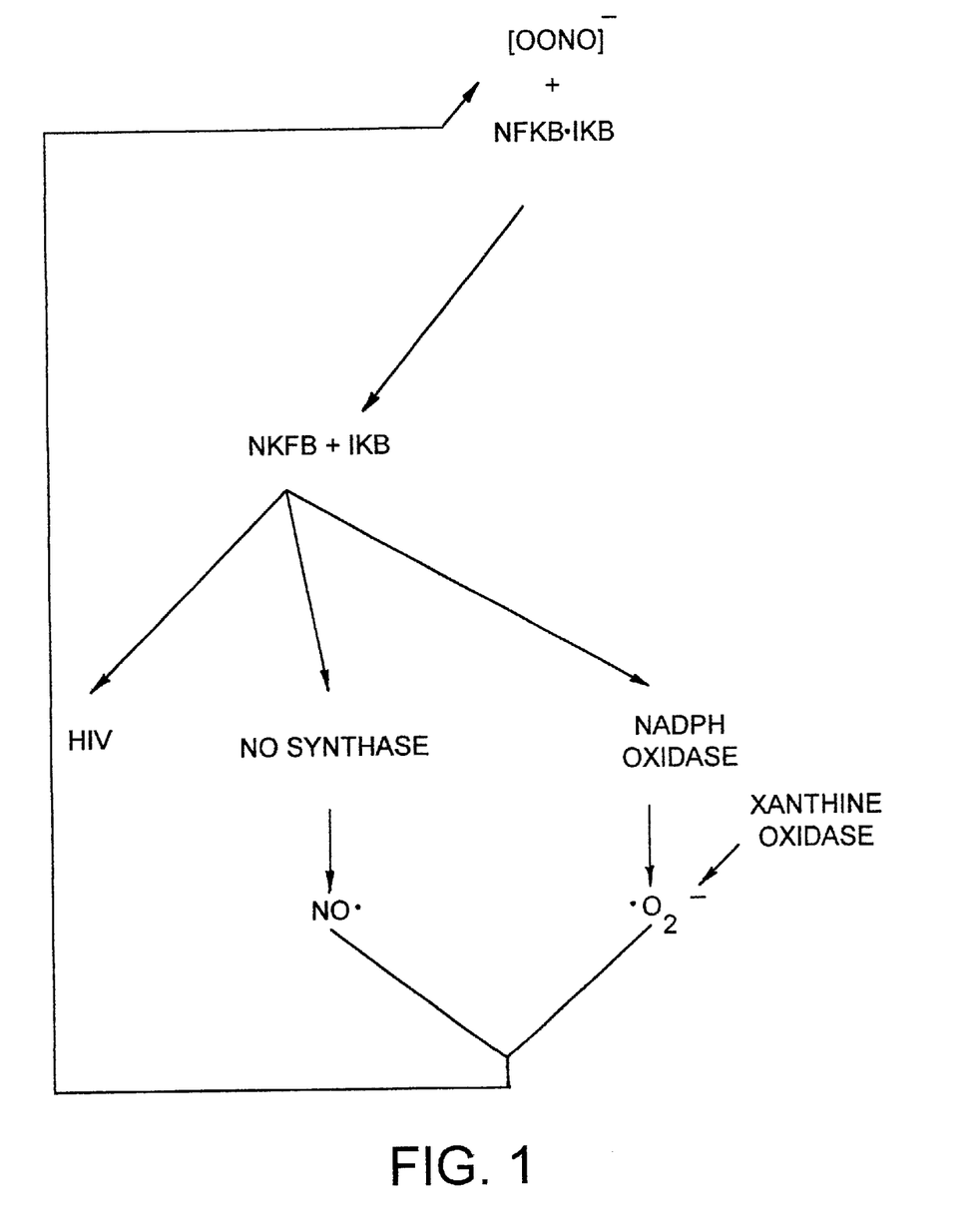
FIG. 1 illustrates the activation mechanism of the HIV virus.

The Role of NFKB and Peroxynitrite in the Activation of a Cell to Reproduce HIV NFKB is a gene transcription factor that switches on the production of the HIV virus of a virally infected cell. NFKB is known to activate a variety of genes, including the transcription of a variety of cytokines, viruses and NO Synthase. The activation of a particular virus, HIV, NO Synthase and NADPH oxidase is shown in FIG. 1.

NO Synthase acts in the cell to produce •NO. NADPH oxidase acts in the cell to produce the superoxide•$O_2^-$. •NO and •$O_2^-$ are combined in the cell to produce peroxynitrite [$OONO^-$] (FIG. 1), the most oxidative material known to be produced by macrophages. Recent work has shown that Kupfer cells of the liver (resident macrophages from blood monocytes) also produce peroxynitrite. This substance is 1,000 times more oxidative than an equivalent molar amount of hydrogen peroxide. In fact, this is the bacterial killing mechanism of the alveolar macrophage.

Studies with black lung disease and silicosis have demonstrated that the alveolar macrophages, activated toward the inflammatory process by instilling silica into animal lungs, produce large amounts of peroxynitrite. This occurs because the nitric oxide synthase of the macrophage is inducible. The presence of silica activates the NO synthase gene to produce much more of the NO synthase enzyme.

Additional studies of maturation and oxidant release in hybridoma macrophages resulted in the observation that the oxidant produced from lipopolysaccharide (LPS) or interferon activated hybridoma macrophages is stimulated about 40 fold using phorbol myristate acetate (PMA). PMA activates the oxidative burst. The oxidant detected is the same oxidant seen in Kupfer liver cells and lung macrophages: peroxynitrite.

Peroxynitrite is significant in that it activates NFKB. NFKB is inactivated by I Kappa B (IKB) which acts on NFKB via the P65 subunit. As shown in FIG. 1, peroxynitrite cleaves IKB, thereby releasing the active NFKB.

The recognition. that peroxynitrite causes the HIV virus and other latent viruses in an infected cell to replicate suggests that inhibition of the oxidation mechanism could stop the replication of the virus. Because all biological systems have built in redundant systems which operate in case of failure of one of the systems, however, it is necessary to use multiple antioxidants simultaneously to block replication of the virus. The use of multiple agents to block a similar metabolic pathway generally produces a synergism between the agents which allows for lower doses of the agents to be given to produce the same results.

Figure 2:
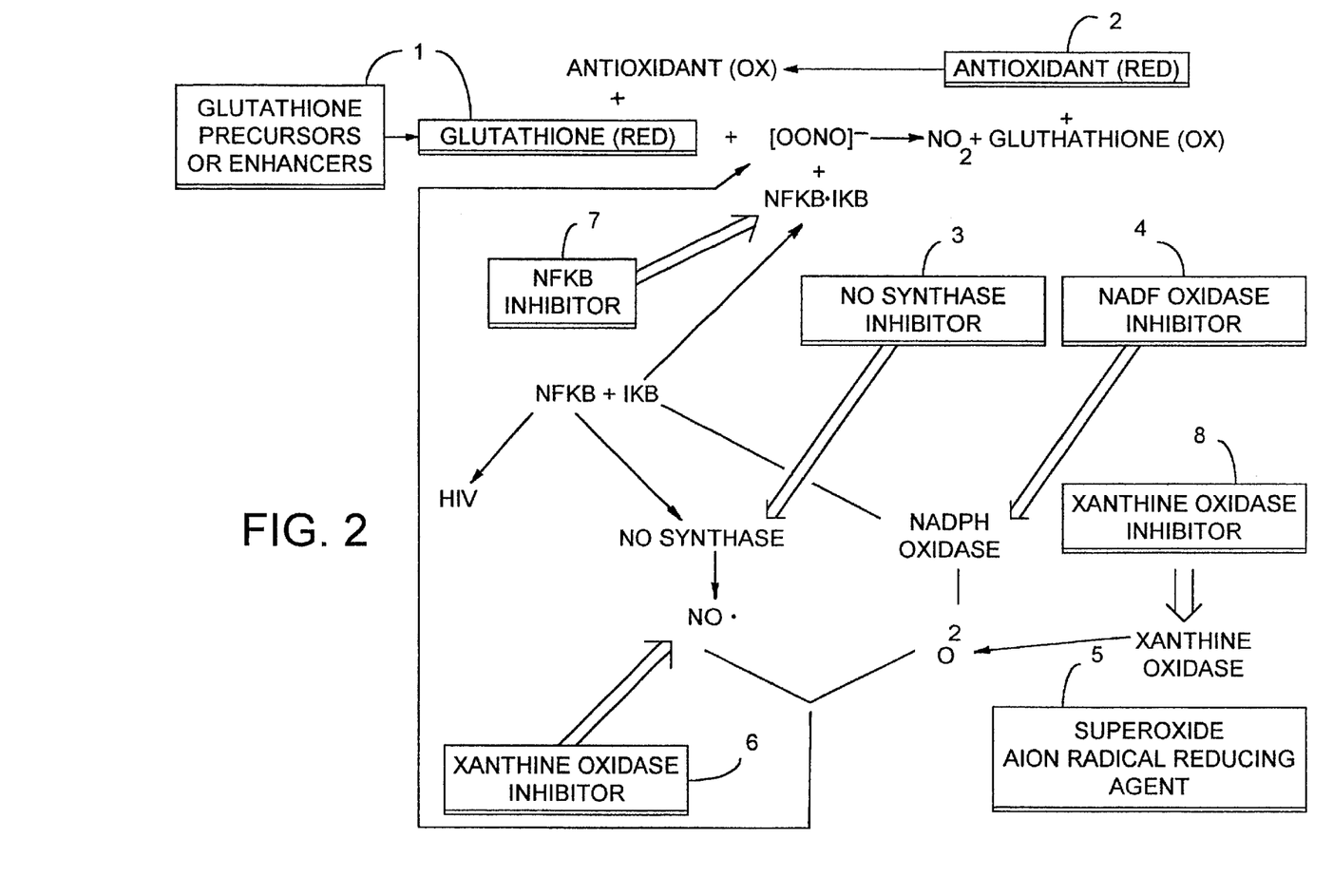
FIG. 2 illustrates various agents and mechanisms for inhibiting viral activation in accordance with the preferred embodiments of the present invention.

The use of multiple synergistic agents to inhibit viral activation is illustrated in FIG. 2. The ingredients administered to or enhanced in the patient in various alternative combinations are shown in boxes in FIG. 2.

Enhancing Reduced Glutathione

The antioxidant mechanism of cells is mainly controlled by reduced glutathione (ingredient 1, FIG. 2), a tripeptide containing L-glutamic acid, L-cysteine and L-glycine. The cysteine contains a sulfhydryl structure which is the antioxidant portion of the peptide. Reduced glutathione reacts with peroxynitrite to reduce it to $NO_2^+$. One aspect of the preferred embodiment of the present invention, therefore, involves the administration of a glutathione agent, such as, but not limited to reduced glutathione, its precursors or its production enhancers.

Since the rate limiting step for the synthesis of reduced glutathione is the concentration of L-cysteine, enhancing blood L-cysteine levels causes blood glutathione levels to increase. N-acetyl cysteine, L-cysteine or 2-oxo-4-thiazolidene carboxylic acid, as well as other substances, can act as glutathione precursors. Since ingestion of large amounts of L-cysteine can produce- toxicity, ingestion of N-acetyl cysteine is preferred. Up to about 40 mg per kilogram of body weight of N-acetyl cysteine can be used daily in man without toxic side effects. N-acetyl cysteine (powder) is available in capsule form. Utilizing a dosage of about 40 mg/kg·day, a 150 pound man can be given about 2,800 mg/day without toxic side effects (150 lbs is approximately 70 kg, 70 kg×40 mg/kg·day equals 2,800 mg/day). If diarrhea occurs after a few days, the dose can be lowered to one-half or one-quarter this amount per day. Doses of about 0.15 to about 0.45 mMol/kg of 2-oxo-4-thiazolidene carboxylic acid can be administered orally without toxicity. In addition, two naturally derived substances ebselen (AS-2) and oltipraz (AS-3) are known to increase the level of glutathione.

Examples of other suitable glutathione precursors besides those already noted include N-acetyl cysteine ester (ethyl or methyl); cystamine (2,2', dithio-bis[ethylamine]); cysteamine; penicillamine; 2,3 dimercapto-1-propanol; L-2-oxothiazolidone-4-carboxylate; diethyl maleate; glutathione esters including mono ethyl, methyl, and isopropyl; and oxazolidone.

The present inventor envisions that in performing the methods of the preferred embodiments, the glutathione, its precursors, or its production enhancers may be administered in bursts of relatively high dosages for limited periods of time. Thus, in administering N-acetyl cysteine, it. may be preferable to utilize much higher doses than 40 mg/kg·day such as about 140 mg/kg·day for a period of several days to a week followed by a reduction in dosage to one-half or one-quarter. It may be desirable to further reduce the dosage to about 10 to about 20 mg/kg·day for 4 to 6 weeks depending upon the length of therapy.

Additional Antioxidants

Additional antioxidants (ingredient 2, FIG. 2), preferably including both water-soluble and fat-soluble antioxidants, are administered for the purpose of regenerating reduced glutathione and/or for the purpose of acting directly on peroxynitrite to reduce it. The level of glutathione is protected by antioxidants such as L-ascorbic acid and Vitamin E in a redox cycle. L-ascorbate (reduced)+glutathione (S—S) (oxidized)→glutathione (SH) (reduced)+L-ascorbate (oxidized). Since the levels of L-ascorbic acid in tissues can be increased greatly by the supply of L-ascorbic acid in blood, ingesting several thousand milligrams of L-ascorbic acid preserves the glutathione in a reduced and active state. Therefore, daily ingestion of N-acetyl cysteine or other glutathione precursors in combination with large amounts of L-ascorbic acid serves to maintain or increase blood glutathione levels in a reduced and active state.

Ascorbic acid or Vitamin C is a unique substance because it is a water-soluble antioxidant that can be taken in doses much larger than the minimal daily requirement (60 mg/day for man). Vitamin C is the most preferred water-soluble antioxidant. If ascorbic acid is taken in doses from about 2,000 to about 10,000 milligrams daily in humans it increases antioxidant content in the blood and cells and protects against strong cellular oxidants like ($OONO^-$). It is most preferred to administer a dosage level of about 2,000 to about 4,000 mg/day of a time release oral dosage, twice daily for the entire length of therapy. These large doses of ascorbic acid are tolerated well by most individuals. It is the only water-soluble antioxidant that can be taken continuously in large doses without major toxicity. It acts not only to protect glutathione (red) as shown in FIG. 2, but also directly against peroxynitrite:

Vit. C+OONO$^-$→Vit. C(OX)+NO$_2^+$+O$_2$

Vitamins A, E and K are fat-soluble compounds which act as antioxidants in the body to oppose peroxynitrite and other strong oxidants that the body may produce. Therefore, these A and K vitamins are used at doses up to about 1 to about 8 times the minimum daily requirement (MDR) in humans, and most preferably about 1 to about 4 times the minimum daily requirement, as set forth in Table 1 below. Vitamin E can be taken at doses of about 3 to about 100 times the MDR, and most preferably about 65 to about 100 times the minimum daily requirement of 30 international units in humans. Vitamin E is the most preferred fat-soluble antioxidant. Vitamin K is taken in smaller amounts and probably plays less of an antioxidant role than Vitamin- A or Vitamin E.

TABLE 1

|  | MDR | Preferred Embodiment | Most Preferred Embodiment |
|---|---|---|---|
| Vitamin A (β-carotene) | 5,000 IU | 5,000–40,000 IU | 5,000–20,000 IU |
| Vitamin E | 30 IU | 90–3,000 IU | 2,000–3,000 IU |
| Vitamin K | 25 mcg | 25–200 mcg | 25–100 mcg |

Minimum daily requirements provide recommendations for daily allowances of a variety of vitamins, nutrients, and minerals. This near universal standard provides a measure of the dosage level for administering the particular vitamins, nutrients, and minerals for humans. Those skilled in the art will readily appreciate that if the methods described herein are performed upon animals other than humans, that appropriate adjustment of the dosage level should be made based upon the body weight of the animal to be treated.

Water-soluble antioxidant minerals such as copper, zinc and iron and selenium are also preferably employed. It is preferred to administer such at doses of about 3 times the minimum daily requirement, as set forth in Table 2 below. The water-soluble antioxidant minerals may be administered in the form of a multivitamin containing minerals. A typical dosage level is 1 tablet per day for the entire period of treatment.

TABLE 2

|  | MDR | Preferred Embodiment |
| --- | --- | --- |
| Copper (as cupric oxide) | 2 mg | 6 mg |
| Zinc (as Zinc oxide) | 15 mg | 45 mg |
| iron (as ferrous salt) | 18 mg | 54 mg |
| selenium (sodium selenate) | 25 mcg | 75 mcg |

A wide array of other antioxidants may be utilized. Most non-steroidal anti-inflammatory drugs function as non-specific antioxidants. Therefore, the best choice would be to use a drug which could react with peroxynitrite but not deplete the glutathione level of cells. Thus ibuprofen would be a good choice while tylenol (acetaminophen) or aspirin (acetyl salicylic acid) would be a poor choice. Other sulfhydryl compounds could be used for this purpose; for example British antilewisite is used as a radio protectant against damage from radioactivity. Its formula is 2,3 dimer-captopropanol or the following structure:

$CH_2\text{-}SH$
$CH_2\text{-}SH$
$CH_2\text{-}OH$

This could be used as an antioxidant against peroxynitrite.

NFKB Induction Inhibitors

NFKB induction inhibitors are agents that inhibit NFKB transcription factor from binding to DNA. This blocks the induction of HIV or other viral reproduction by directly suppressing the viral reproduction activating mechanism. NFKB inhibitors (item 7, FIG. 2) also suppress peroxynitrite synthesis, by preventing NFKB from activating cell genes to produce NO synthase.

While ingestion of L-cysteine precursors or antioxidants like vitamins C, E and A, support the activity of glutathione against peroxynitrite, synergistic benefits are obtained by also attacking the biochemical pathways by which peroxynitrite is synthesized. Macrophages and T lymphocytes need nitric oxide and superoxide to produce peroxynitrite. Therefore, inhibition of NO synthase (see ingredient 3, FIG. 2), which produces nitric oxide, and inhibition of NADPH oxidase (see ingredient 4, FIG. 2), which produces superoxide, either alone, or in combination can inhibit the production of peroxynitrite.

NO synthase can be inhibited by anti-inflammatory steroids because they block NO synthase induction. Pyrrolidine dithiocarbamate suppresses peroxynitrite by acting as an antioxidant against peroxynitrite. The NO synthase produces nitric oxide which together with superoxide produces peroxynitrite ($OONO^-$). If the excessive •NO is not produced then the peroxynitrite is not produced and the activation of the viral protease which splits the inhibitory factor (i Kappa B) n F-Kappa B from the tricomplex of p50, p65 and i Kappa B does not happen. Once the NO synthase within the macrophage has been induced (30–40 fold sometimes) it is very difficult to control the amount of peroxynitrite that is produced (an ounce of prevention is worth a pound of cure).

The preferred type of NFKB induction inhibitor is an anti-inflammatory steroid. Examples of suitable anti-inflammatory steroids suitable as NFKB induction inhibitors include but are not limited to predonsone, prednisolone, methyl prednisolone, dexamethasone, beta metasone dehydroepiandrosterone, 9a-fluorocortisol, prednisone, aetiocholanolone, 2-methylcortisol, pregnanediol, deoxycorticosterone, cortisone, hydrocortisone (cortisol), 6a-methylprednisolone, triamcinolone, estrogen or derivatives thereof. Generally, any steroid with anti-inflammatory action toward NFKB may be used. In addition, one or more suitable nonglucocorticoid lazaroids may be utilized as NFKB induction inhibitors. Preferred lazaroids include, but are not limited to, U-74006F, which is 21-[4-(2,6-di-1-pyrrolidinyl-4-pyrimidinyl)-1-piperazinyl]-16-methyl-(16.alpha.)-pregna-1,4,9(11)-triene-3,20-dione monomethanesulfonate or TIRILAZAD mesylate or Free-dox; U-74389G, which is 21-[4-(2,6-di-1-pyrrolidinyl-4-pyrimidinyl)-1-piperazinyl]-pregna-1,4,9(11)-triene-3,20-dione, (Z)-2-butenedioate (1:1); U-74500A which is pregna-1,4,9(11)-triene-3,20-dione, 21-[4-[5,6-bis(diethylamino)-2-pyridinyl]-1-piperazinyl]-16-methyl-, hydrochloride, (16.alpha.); U-75412E which is 21-[4-[3-(ethylamino)-2-pyridinyl]-1-piperazinyl-16-methyl-pregna-1,4,9(11)-trien-3,20-dione, (16.alpha.)-,(Z)-2-butenedioate (1:1); U-78517F which is 2-[[4-(2,6-di-1-pyrrolidinyl-4-pyrimidinyl)-1-piperazinyl]-methyl]-3,4-dihydro-2,5,7,8-tetramethyl-2H-1-benzopyran-6-ol, dihydrochloride; U-78517G which is 2H-1-benzopyran-6-ol, 2-[[4-(2,6-di-1-pyrrolidinyl-4-pyrimidinyl)-1-piperazinyl]methyl]-3,4-dihydro-2,5,7,8-tetramethyl-, 2-hydroxy-1,2,3-propanetricarboxylate (1:2); U-78518E which is 2H-1-benzopyran-6-ol, 2-[[4-[3-(ethylamino)-2-pyridinyl]-1-piperazinyl]methyl]-3,4-dihydro-2,5,7,8-tetramethyl-, hydrochloride; U-79206 which is ethanol, 2-[(2,6-di-1-pyrrolidinyl-4-pyrimidinyl) methylamino]-; and U-83836E which is (−)-2-[[4-(2,6-di-1-pyrrolidinyl-4-pyrimidinyl)-1-piperazinyl]methyl]-3,4-dihydro-2,5,7,8-tetramethyl-2H-1-benzopyran-6-ol, dihydrochloride. These lazaroids may be administered in single intravenous doses ranging from about 0.1 to about 10.0 mg per kilogram of body weight, or in single oral doses of from about 1 to about 30 mg per kilogram of body weight for every day of therapy. An exemplary listing of suitable commercially available steroids and corresponding suppliers is set forth below in Table 3:

TABLE 3

| Drug | Trade Name | Length of Action | Company |
| --- | --- | --- | --- |
| Dexamethasone | DECADRON | long | Merck |
| Methyl prednisolone | DOSE PAK | short | Upjohn |
| Methyl prednisolone[1] | DEPO-MEDROL | very long | Upjohn |
| Triamcinolone | — | short or intermediate | Fujisama |
| Cortisone | CORTONE | short | Generic |
| Prednisone | DELTASONE | short | Generic |

Generally these drugs are best used when a short acting glucocorticoid steroid like prednisone, prednisolone, methyl prednisolone and esters can be given in the following manner similar to a dose-pack procedure for poison ivy (each tablet is approximately 4 mg).

| | |
|---|---|
| 6 tablets | first day |
| 5 tablets | second day |
| 4 tablets | third day |
| 3 tablets | fourth day |
| 2 tablets | fifth day |
| 1 tablet | sixth day |

In accordance with the preferred embodiment, this is used on a continuous basis, that is administering 1–4 tablets per day in conjunction with antioxidants over the duration of treatment until the person is assayed HIV negative using antibody and/or ELISA procedure. If methyl prednisolone (4 mg/tablet) is used this would be the procedure. This according to PURAMED pharmaceuticals, Cincinnati, Ohio 45213 (NDC 51285-30121). DEPO-MEDROL (methyl prednisolone) can be injected every two weeks intramuscularly at 40 milligrams per kilogram of body weight. Other anti-inflammatory steroids can be substituted at appropriate doses, as set forth in the *Physicians' Desk Reference*. Adminstration of an NFKB induction inhibitor such as an anti-inflammatory steroid, is one of the most important steps in the treatment of HIV, AIDS related infection. However, it is to be used with caution in later stages of AIDS disease. The actual dose of steroid may vary with the state of the disease and the person, therefore dose ranges are given.

Other short acting inflammatory steroids such as hydrocortisone and cortisone may be administered at dosages of preferably about 100 mg/day per person for the first week of therapy. After that, dosage levels may be reduced to about 15 mg/day to about 25 mg/day per person for the duration of treatment.

Long or intermediate acting glucocorticoids like dexamethasone and triamcinolone could be used to inhibit the induction of NO synthase but they could produce more long term suppression of the adrenal steroid output causing the possibility of adrenal insufficiency. For a long acting steroid such as dexamethasone, it is preferred to administer a dosage of about 10 mg/day per person for the first week of treatment. After that, the dosage may be reduced to about 2 mg/day to about 5 mg/day per person for as long as treatment continues. For intermediate acting steroids, preferred dosage levels are about 50 mg/day per person for the first week of treatment followed by a reduction to about 10 mg/week to about 20 mg/week for the duration of treatment.

In addition, to the previously noted anti-inflammatory steroids and lazaroids, a variety of other compounds may be utilized as NFKB induction inhibitors such as pyrrolidine dithiocarbamate and other dithiocarbamates, and glycyrrhizic acid (from licorice root). A preferred dosage level when administering glycyrrhizic is about 100 mg/day per person for each day of therapy. In addition, other compounds are suitable for use as NFKB induction inhibitors. These inhibitors include, but are not limited to, immunosuppressants such as cyclosporin A, rapamycin, interleukin 10, and FK 506. FK 506 is available from Merck. Interleukin 10 appears to have an effect similar to the combination of anti-inflammatory steroids and antioxidants. Clearly, a wide array of plant steroids, male steroids, female steroids, glucocorticoids, lazaroids, and 21-aminosteroids are eligible for use as NFKB induction inhibitors.

An inhibitor known to be effective against NFKB binding or expressing is mevinolin, a drug which prevents isoprenylation and methylthioadenosine (MTA) and inhibitor of several S adenosylmethionine dependent methylation reactions.

Optional Peroxynitrite Production Suppressors

Superoxide which is necessary to producing peroxynitrite, can be inhibited using RAC antisense nucleotides against the gene system producing superoxide. Dorseuil et al., *J. of Biol. Chem.*, 267:20540, 1990, report that RAC. protein content of lymphocytes decreased 60% in RAC antisense pretreated cells and superoxide production decreased 50–60% in a dose dependent manner in antisense pretreated lymphocytes. This demonstrates a physiological role of RAC proteins in inhibition of NADPH oxidase. Other NADPH oxidase inhibitors include diphenyl iodonium o diphenylene iodonium ($1.5 \times 10^{-8}$M) or diphenylene iodonium bisulfate; 17 hydroxy wortmannin (HWT), a fungal metabolite; Okadaic acid; alpha-1-antichymotrypsin; staurosporine; Ebselen-[2-phenyl-1,2-b en3isoselanazol-3[2H]one]; and apocynin (4-hydroxy-3 methoxyacetophenone).

Superoxide can be produced at the membrane of certain cells (neutrophil, macrophages, etc.) by NADPH oxidase system using $O_2$ and various cofactors. When xanthine oxidase catalyzes the oxidation of xanthine and hypoxanthine, it also produces superoxide anion $[.O_2]$. Since superoxide can be reacted with nitric oxide to produce $(OONO^-)$ peroxynitrite, inhibiting the production of superoxide by any source or scavenging its activity would be important. Drugs like allopurinol and its metabolite oxypurinol are known to inhibit xanthine oxidase (ingredient 8, FIG. 2) as well as to function as antioxidants against peroxynitrite.

Rather than inhibiting NADPH oxidase, any superoxide produced can be reduced to hydrogen peroxide by using a superoxide reducing agent (ingredient 5, FIG. 2) such as an enzyme called Cu, Zn superoxide dismutase (SOD). This enzyme is injected into the blood stream. Because the enzyme has a short half-life in the blood, conjugation with polyethyleneglycol prolongs the half-life of SOD. IgA SOD and liposome encapsulated SOD have also been found to have prolonged circulating half-life compared to native SOD. Further, SOD mimics might also be useful because they penetrate cells where SOD has some difficulty. These are compounds that may have copper, zinc or the combination of these elements but without the amino acids (protein portion). SOD cannot penetrate cells to scavenge superoxide is inside a cell but the superoxide dismutase mimics could penetrate cells and act by destroying superoxide inside cells. Examples of such SOD mimics are given in Yaping, T. et al.: The Inhibitory Effect of 21 Mimics of SOD; Inhibition of Superoxide Formation. *Free Rd. Biol. Med.*, 13:533–541, 1992.

NO reducing agents can also be used to minimize production of peroxynitrite (see item 6, FIG. 2). These agents might also be thought of as binders, e.g., hemoglobin or methylene blue.

Proposed Mechanisms of the Preferred Embodiments

Figure 3:
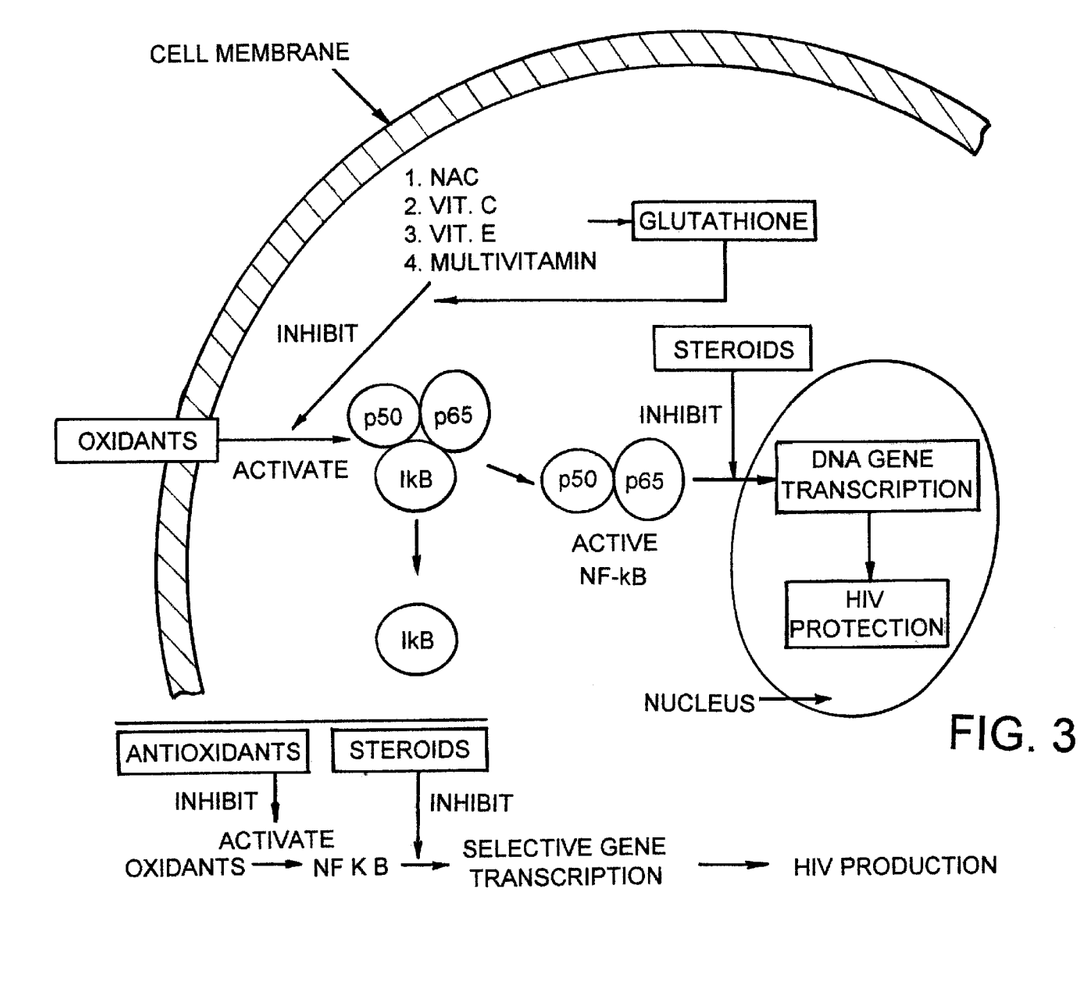
FIG. 3. illustrates the roles of antioxidants, a glutathione agent, and steroids in the preferred embodiments of the present invention.

Although not wishing to be bound to any particular theory, FIG. 3 illustrates the mechanisms theorized as to the role of antioxidants, glutathione agents, and steroids with regard to HIV production. HIV replication is blocked by a combination of antioxidants and NFKB induction inhibitor. About 70% of the blocking action of HIV replication is believed to stem from the NFKB induction inhibitor, which preferably is one or more anti-inflammatory steroids. Although such steroids do not have direct inhibitory activity, they control viral synthesis by blocking NFKB induction. As will be recalled, NFKB is a DNA transcription factor made of protein. NFKB controls a whole series of inflammatory cytokines and NO synthase as well as HIV and FIV replication. Upon introduction of steroids to the biological system, steroids shut off or block about 70% of HIV or other viral production depending upon the dose of steroids, of HIV, cytokines, and NO synthase.

However, for NFKB to be active it must shed its inhibitory factor I kappa B. Such shedding requires oxidation because the bonds holding the inhibitory factor to proteins P50 and P65 are sensitive to oxidation. Thus, antioxidants keep the I kappa B inhibitory factor bound to NFKB and therefore inactive. The role of antioxidants in the mechanism depicted in FIG. 3 is believed to be responsible for about 30% of the activity of producing NFKB, and preventing HIV replication.

All the components noted herein are administered to the animal in need of treatment by any means known to those skilled in the art. Although it is most preferred to administer the anitoxidants including glutathione agent and NFKB induction inhibitor concurrently, or simultaneously, it is not a requirement. Thus, the preferred embodiments of the present invention also encompass administering the various components separately, and over a period of time so long as the synergism stemming from their combined presence or mechanisms still occurs. Thus the components are administered generally concurrently, such that they are present in the animal system concurrently. Modes of administration include but are not limited to oral administration and injection, such as intramuscular injection.

Pharmaceutical Compositions and Kits

The present invention also provides pharmaceutical compositions for use in repressing the reproduction of latent viruses or retroviruses such as HIV. The preferred embodiment compositions comprise mixtures of the above described components with the ususal pharmaceutical carriers and diluents. Thus, a preferred embodiment composition comprises: (1) a glutathione agent; (2) an effective amount of one or more additional antioxidants; and (3) an effective amount of an NFKB induction inhibitor. In a most preferred embodiment, the pharmaceutical compositions comprise: (1) an effective amount of a glutathione agent, e.g. glutathione, a glutathione precursor, and/or a glutathione production enhancer, (2a) an effective amount of a water-soluble antioxidant, (2b) an effective amount of a fat-soluble antioxidant, and (3) an effective amount of an anti-inflammatory steroid as the NFKB induction inhibitor. The other ingredients described above may also be included.

Pharmaceutical compositions in accordance with the preferred embodiment described herein may be administered orally (in the form of tablets, capsules or solutions) or parenterally (in the form of injections or pellets). These preparations can be made by usual methods using common carriers and excipients. For tablets, for example, water, glucose, maltose, gum arabic, gelatin, mannitol, starch paste, magnesium trisilicate, talc, corn starch, colloidal silicate, potato starch and urea are used as carriers and excipients. Solutions include aqueous or oily suspensions, syrup and elixirs, which can be prepared by commonly used techniques.

Moreover, the present invention provides pharmaceutical kits that contain the ingredients of the pharmaceutical composition described herein, however, packaged individually. That is, a kit is provided that contains a supply of antioxidants, preferably a water-soluble antioxidant and a fat-soluble antioxidant, a supply of a glutathione agent and a supply of an anti-inflammatory steroid. The user then administers, preferably generally concurrently, the ingredients. The other ingredients. described above may also be included.

Applications of the Preferred Embodiment Methods, and Compositions

In addition to the treatment of humans, the treatment methods of the preferred embodiments are particularly well suited for treatment of birds such as turkeys and chickens. These birds are prime targets for AIDS or immunodeficiency virus as whole flocks may be killed at one time. The treatments could be administered to fowl by introduction in feed. A wide variety of other animals are known to be infected by retroviruses and so could be treated according to the methods described herein. Cattle are known to be infected by bovine viruses. Primates such as monkeys, apes and macaques can be infected by simian immunodeficiency virus. Cats, of nearly all varieties such as lions, tigers, house cats, pumas, leopards, cheetahs and panthers, can be infected by feline immunodeficiency virus. Sheep and goats can be infected by visna-maedi. Horses can be infected by equine infectious anemia. Moreover, other animals may be infected by retroviruses such as rats, mice, pigs, dogs, minks, marine animals such as sea lions and sockeye salmon and river salmon. All treatments described or taught herein may be performed upon other animals than those described by appropriate adjustments to dosages according to animal body weight.

The embodiments described herein may be employed for treating a wide array of viruses, including retroviruses. Examples of such viuses include, but are not limited to, Abelson murine leukemia virus, Adult T cell leukemia virus, AKR murine leukemia virus, Avian acute leukemia virus, Avian erythroblastosis virus, Avian Influenza virus, Avian leukemia sarcoma virus, Avian leukemia virus, Avian leukosis virus, Avian mycloblastosis virus, Avian sarcoma virus, Avian sarcoma-leukemia virus, Baboon endogenous retrovirus, Bovine immunodeficiency. virus, Bovine leukemia virus, Bovine synctial virus, Bovine syncytium forming virus, Caprine arthritis encephalitis virus, Chick synctial virus, Chicken synctial virus, Duck infectious anemia virus, Equine infectious anemia virus, FBJ murine osteogenic murine sarcoma virus, FBJ murine sarcoma virus, Feline immunodeficiency virus, Feline leukemia virus, Feline sarcoma virus, Feline syncytium forming virus, Foamy viruses, Friend murine leukemia virus, Friend spleen focus forming virus, Fujinami sarcoma virus, Gardner—Rashed feline sarcoma virus, Gibbon ape leukemia virus, Gross virus, Hamster synctium forming virus, Hardy-Zuckerman feline sarcoma virus, Harvy murine sarcoma virus, Human immunodeficiency I, Human immunodeficiency II, Human immunodeficiency virus, Human spuma virus, Human T cell leukemia virus, Human T cell leukemia virus type I, Human T cell leukemia virus type H, Human T cell leukemia virus type III, Kirsten murine sarcoma virus, Lentiviruses (general terms), Mason pfizer monkey virus, Mink cell focus forming murine leukemia virus, Mo T cell virus, Moloney murine leukemia virus, Moloney murine sarcoma virus, Mouse mammary tumor virus, Murine parvo virus, Myeloblastosis associated virus, Myelocytomastosis virus 29, Myeloproliferative sarcoma virus, Murine leukemia virus, Murine parvovirus, Oncoviruses, Oregon sockeye salmon disease virus, PO-I-Lu virus, Rabbitpox papilloma virus, Reticuloendotheliosis strain T, Reticuloendotheliosis-associated, Rous sarcoma virus, Sacramento River Chronic Disease (Salmon), Sea lion foamy virus, Simian foamy virus, Simian immunodeficiency, Simian retrovirus type I, Simian retrovirus type II, Simian retrovirus type III, Simian retrovirus type IV, Simian retrovirus type V, Simian sarcoma associated virus, Simian sarcoma virus, Simian T cell leukemia virus, Simian T cell leukemia virus type III, Simian T lymphoma virus I, Snyder-Thelin feline sarcoma virus, South African ovine macdi-visma virus, Spleen focus forming virus, Spima virus, Spimavirus, Squrrel monkey retrovirus (Aotus), and Spuma-Maedi virus.

EXAMPLES

In vivo testing was performed to demonstrate the startling effectiveness of the treatment methods described herein. A series of laboratory tests were conducted on retrovirus-infected cats. In the preferred treatment regimen, the animal suffering from HIV(+), is administered relatively large doses of both water-soluble and fat-soluble antioxidants such as Vitamins C, A and E; an effective amount of at least one glutathione precursor such as N-acetyl cysteine; followed by an NFKB induction inhibitor such as one or more anti-inflammatory steroids or lazaroids. As summarized. in Table 4 below, seven cats heavily infected with HIV or FIV were treated according to the methods described and claimed herein. Each cat weighed approximately 10 to about 18 pounds. The cats were initially treated with a single dosage of an effective amount of an NFKB induction inhibitor, that is an anti-inflammatory steroid dose of DEPO-MEDROL (20–25 mg) and a series of oral dosages of a glutathione precursor, N-acetyl cysteine. The amount of N-acetyl cysteine administered with food to each cat was 1,200 mg per day. In addition, large dosages of fat-soluble and water-soluble antibxidants, Vitamins E, C, and A were administered to the cats orally every day by mixing in cat food. Vitamin E was administered at a dosage of 400 IU per day to each cat and Vitamin C was administered at a level of 500 mg per day to each cat. Vitamins A, K, and copper and zinc were also administered via 1 PET TABS per day to each cat. PET TABS is a commercially available multivitamin for pets such as cats, and is available from Smith-Kline Beecham.

The treated cats: were monitored by ELISA assay for feline leukemia viruses antigen/feline immunodeficiency virus antibody test (CITE PRO COMBO: Programmed Biodetection available from IDEXX Corp. of Portland, Me.) for about two weeks. Of the seven cats tested, all seven appeared to have been cured from their earlier infection of feline leukemia, feline AIDS or both. The treatment process lasted one to two months of continual treatment with N-acetyl cysteine and high dosages of Vitamins C, E and A and periodic administration of anti-inflammatory steroids.

TABLE 4

EFFECT OF ANTIRETROVIRAL THERAPY ON RETROVIRUS-INFECTED CATS

| Age | Sex | Name | Assay | Symptoms | Assay |
|---|---|---|---|---|---|
| 8 | F | Champagne | FELV(+), FIV(+) | hair loss, lost teeth | FELV(−), FIV(−) |
| 8 | M | Precious | FELV(+), FIV(+) | vomiting, dental problems | FELV(−), FIV(−) |
| 9 | F | Missy | FELV(+), FIV(+) | Bloody diarrhea, problems dental | FELV(−), FIV(−) |
| 11 | M | Sampson | FIV(+) | vomiting, gum red | FIV(−) |
| 8 | M | Josey | FELV(+) | teeth loss, no appetite, lung problem | FELV(−) |
| 10 | M | Patch | FIV(+) | poor appetite, lethargy | FIV(−) |
| 12 | M | Bud | FIV(+) | weight loss, no appetite | FIV(−) |

Notes
1) One cat with FELV(+)/FIV(+) died without the treatment as a control.
2) Treatments: Cats were injected intramuscularly with 20 mg DEPO-MEDROL (anti-inflammatory steroid) and dispensed with 1,200 mg powdered N-acetyl cysteine, 200 IU of Vitamin E, 500 mg of Vitamin C and one PET TAB/day.
3) It takes from 3 weeks to 6 weeks for the cats to turn retrovirus positive reaction to negative after the treatment.
4) The symptoms of Champagne, Precious, and Missy such as dental problems, bloody diarrhea, and loss of appetite completely subsided after the treatment with steroids/antioxidants. The symptoms of Sampson such as vomiting, gum disease, and loss of appetite completely reversed after the treatment. Josey's symptoms of lung problem, loss of appetite, and gum infection cleared up following the treatment. The cats were maintained on PET TABS following the treatment with steroid/antioxidants.
5) At the conclusion of the test all cats remained FIV or leukemia virus negative.
6) Blood was drawn for analysis from four of the cats treated (Sampson, Josey, Patch, and Bud). The analysis included cell cultures, mitogen stimulation, and polymerase chain reaction assay for the retrovirus. All tests indicated the cats were fully cured as none indicated any sign of the virus.

These cat experiments are the first to demonstrate that AIDS can be cured in an in vivo model. Treatments were performed by a licensed veterinarian. The treatment methods were also performed by a second veterinarian. The second set of treatments were also successful.

In an optional treatment regimen, to be followed when the animal suffering from HIV(+), is exhibiting AIDS (that is, a T-lymphocyte or $CD_4$ lymphocyte count less than 100 cells/mm$^3$), relatively large doses of both water-soluble and fat-soluble antioxidants and an effective amount of at least one glutathione precursor such as N-acetyl cysteine are administered. Before an NFKB induction inhibitor is administered, the $CD_4$ (T-lymphocyte) count is increased to about 100 cells/mm$^3$ or more. The $CD_4$ count may be raised by administering, such as by injection, GM-CSF to stimulate monocytes. GM-CSF is a granulocyte monocyte cell stimulating hormone. Alternatively, or in addition to administering GM-CSF, fresh white cell concentrates containing monocytes may be given, such as via transfusions. Once $CD_4$ counts are about 100 cells/mm$^3$ or more, an NFKB induction inhibitor is administered.

In both the preferred and optional treatment regimens, the NFKB induction inhibitor is administered until AIDS(−) is indicated from AIDS(+) blood assay, via ELISA, Western blot, and PCR (polymerase chain reaction) analyses. It is also preferred to administer in conjunction with the antioxidants, a daily multivitamin containing all recommended minerals with copper and zinc. The administration of GM-CSF and/or transfusion of fresh white cell concentrates containing monocytes may be performed simultaneously or in conjunction with the administering of multivitamins, water-soluble antioxidants, fat-soluble, antioxidants and/or glutathione precursor.

The following is a description of exemplary treatment methods for humans in accordance with the preferred embodiment.

Human patients are divided into two groups:
1. Group 1 with HIV(+) but no AIDS (T-lymphocyte, i.e., $CD_4$ lymphocyte count equal to or more than 200 cells per cubic millimeter).
2. Group 2 with AIDS.

The Group 1 HIV(+) patients with AIDS, are treated as follows.

Each patient is administered:
1. One daily multivitamin with a complete array of recommended minerals, Vitamin A, a beta carotene content of 4–8 times normal, and effective amounts of copper and zinc.
2. Vitamin E at a dosage level of 2000 IU/day.
3. Vitamin C at a dosage level of 3,000 mg/day.
4. N-acetyl cysteine at a dosage level initially at about 140 mg/kg per day, and gradually reduced to a level of about 40 mg per kilogram of body weight, every day.
5. Methyl prednisolone at a dosage level of 4–16 mg per day or 40 mg DEPO-MEDROL injected every two weeks intramuscularly (fleshy areas, e.g., deltoid), per kilogram of body weight. DEPO-MEDROL was administered since it utilizes a slow release form of methyl prednisolone.

Preferably, components 1–5 are administered simultaneously throughout the treatment period. Treatment is continued until an AIDS(−) blood assay based on ELISA, Western blot, and PCR (polymerase chain reaction) techniques is obtained. It is clearly envisioned that dosage levels of A, E, C, N-acetyl cysteine, and methyl prednisolone or other steroids or lazarbids could be administered at levels described elsewhere herein. Moreover, it is also envisioned that other suitable glutathione precursors could be utilized in place of, or instead of the N-acetyl cysteine. Similarly, one or more other NFKB induction inhibitors could be utilized in place of or instead of the methyl prednisolone.

The second group of HIV(+) patients, with AIDS, is treated the same as the first group, with the exception that the administration of the anti-inflammatory steroid, methyl prednisolone; is added with GM-CSF (granulocyte monocyte cell stimulating hormone) until the $CD_4$ (T-lymphocyte) count is at least 200 cells per cubic millimeter. This is accomplished either by: injection with GM-CSF to stimulate monocytes, or transfusion to give fresh white cell concentrates containing monocytes. Once the $CD_4$ counts are increased to around normal, the administration of the GM-CSF is discontinued. Treatment is continued until an AIDS(−) blood assay based on ELISA, Western blot, and PCR-techniques is obtained.

To date, the preferred embodiment methods have been carried out on one human subject infected with HIV and exhibiting AIDS. Prior to treatment, the subject had a $CD_4$ cell count of 44 to 49. After a three-month treatment period, the subject's $CD_4$ cell count increased to 180. In addition, all other diseases that the subject was suffering from, AIDS dementia, herpes infection and fungal infection were either eliminated or brought under control after the three-month treatment period. This treatment was without GM-CSF.

The present inventor envisions a wide array of treatments that are variations of the preferred embodiments described herein. For instance, it has been discovered that Herpes viruses are effectively treated by a treatment regimen comprising, administering generally concurrently, (1) at least one glutathione agent, (2) at least one water soluble antioxidant at doses higher than the recommended daily minimum requirements, (3) at least one fat soluble antioxidant at doses higher than the recommended daily minimum requirements, and preferably, only slight amounts or no NFKB induction inhibitor. In a most preferred treatment regimen, the subject suffering from symptoms of the Herpes virus is administered generally concurrently, (1) at least one glutathione agent, (2) Vitamin C at doses higher than the recommended daily minimum requirements, and (3) Vitamin E at doses higher than the recommended daily minimum requirements. The dosage levels for (1), (2), and (3) are in accordance with the previous teachings herein. Also related to these preferred treatment methods are pharmaceutical compositions and kits for treating Herpes comprising (1) at least one glutathione agent, (2) at least one water soluble antioxidant, and (3) at least one fat soluble antioxidant. The amounts or proportions of each are in accordance with the teachings herein. This treatment has been found to be surprisingly effective in preventing the reproduction of the Herpes virus.

Of course, it is understood that the foregoing are merely preferred embodiments of the invention and that various changes and alterations can be made without departing from the spirit and broader aspects thereof as set forth in the appended claims, which are to be interpreted in accordance with the principles of patent law including the Doctrine of Equivalents.

The embodiments of the invention in which an exclusive property or privilege is claimed are defined as follows:

1. One of a pharmaceutical composition and kit comprising:
   (i) an agent in an amount effective to cause blood glutathione levels to increase, selected from the group consisting of glutathione, N-acetyl cysteine, 2-oxo-4 thiazolidine carboxylic acid, ebselen, oltipraz, L-cysteine, N-acetyl cysteine ethyl ester, N-acetyl cysteine methyl ester, cystamine, cysteamine, penicillamine, 2,3 dimercapto-1-propanol, L-2-oxothiazolidone-4-carboxylate, dimethyl maleate, glutathione ethyl ester, glutathione methyl esters, glutathione isopropyl ester, oxazolidone, and combinations thereof;
   (ii) an amount of one or more additional antioxidants at a dose higher than the recommended daily minimum requirement; and
   (iii) an NFKB induction inhibitor in an amount effective to inhibit nuclear factor kappa B, said NFKB induction inhibitor being selected from the group consisting of anti-inflammatory steroids and nonglucocorticoid lazaroids.

2. The composition or kit of claim 1 wherein said additional antioxidants comprise at least one member selected from the group consisting of a water-soluble antioxidant, a fat-soluble antioxidant, and combinations thereof.

3. The composition or kit of claim 2 wherein said additional antioxidant is a water-soluble antioxidant.

4. The composition or kit of claim 3 wherein said additional water-soluble antioxidant is Vitamin C.

5. The composition or kit of claim 2 wherein said additional antioxidant is at least one fat-soluble antioxidant.

6. The composition or kit of claim 5 wherein said fat-soluble antioxidant is selected from the group consisting of Vitamin E, Vitamin K, Vitamin A, and combinations thereof.

7. The composition or kit of claim 1 in which said agent which causes blood glutathione levels to increase is N-acetyl cysteine.

8. The composition or kit of claim 1 wherein said NFKB induction inhibitor comprises an anti-inflammatory steroid.

9. The composition or kit of claim 8 wherein said anti-inflammatory steroid is selected from the group consisting of predonsone, prednisolone, methyl prednisolone, dexamethasone, beta metasone dehydroepiahdrosterone, 9a-fluorocortisol, prednisone, aetiocholanolone, 2-methylcortisol, pregnanediol, dexycorticosterone, cortisone, hydrocortisone, 6a-methylprednisolone, triamcinolone, estrogen, and combinations thereof.

10. The composition or kit of claim 1 in which said NFKB induction inhibitor is methyl prednisolone.

* * * * *

UNITED STATES PATENT AND TRADEMARK OFFICE
CERTIFICATE OF CORRECTION

PATENT NO. : 6,514,955 B1
DATED : February 4, 2003
INVENTOR(S) : Knox Van Dyke

It is certified that error appears in the above-identified patent and that said Letters Patent is hereby corrected as shown below:

Column 1,
Lines 7 and 8, "PRODUCTION" should be -- REPRODUCTION --.

Column 3,
Line 4, "fHIV" should be -- HIV --.

Column 5,
Line 30, "produce-" should be -- produce --.

Column 6,
Line 44, "Vitamin- A" should be -- Vitamin A --.

Column 8,
Line 24, "after "piperazinyl" insert -- ] -- before "-16-methyl".
Line 61, insert -- [1]DEPO-MEDROL: intramuscular injection every 5-10 days, and slow release form. --.

Column 9,
Line 52, "glycyrrhizic" should be -- glycyrrhizin --.

Column 10,
Line 6, after "RAC" delete "." (period).
Line 12, "o" should be -- or --.
Line 44, after "superoxide" delete -- is --.
Line 22, "[.O$_2$]_." should be -- [●O$_2$]_. --.

Column 11,
Line 2, "FIV replication" should be -- HIV replication --.

Column 12,
Line 3, after "ingredients" delete "." (period).
Line 39, after "immunodeficiency" delete "." (period).
Line 55, "type H" should be -- type II --.

Column 13,
Line 8, "Squrrel" should be -- Squirrel --.
Line 23, after "summarized" delete "." (period).
Line 34, "Antibxidants" should be -- antioxidants --.

UNITED STATES PATENT AND TRADEMARK OFFICE
CERTIFICATE OF CORRECTION

PATENT NO. : 6,514,955 B1
DATED : February 4, 2003
INVENTOR(S) : Knox Van Dyke

It is certified that error appears in the above-identified patent and that said Letters Patent is hereby corrected as shown below:

Column 15,
Line 35, "lazarbids" should be -- lazaroids --.

Column 16,
Line 41, "methyl esters" should be -- methyl ester --.

Column 17,
Line 6, "dehydroepiahdrosterone" should be -- dehydroepiandrosterone --.

Signed and Sealed this

Twelfth Day of August, 2003

JAMES E. ROGAN
*Director of the United States Patent and Trademark Office*